United States Patent [19]

Stahl

[11] Patent Number: 5,019,036
[45] Date of Patent: May 28, 1991

[54] METHOD AND APPARATUS FOR REMOVING GELATINOUS TISSUE

[76] Inventor: Norman O. Stahl, 3199 Monterey Dr., Merrick, N.Y. 11566

[21] Appl. No.: 441,971

[22] Filed: Nov. 28, 1989

[51] Int. Cl.$^5$ .............................................. A61B 17/32
[52] U.S. Cl. ....................................... 604/22; 606/170
[58] Field of Search .............. 606/170, 171, 180, 159; 604/22; 30/29.5, 43.6; 128/751, 752

[56] References Cited

U.S. PATENT DOCUMENTS

| | | | |
|---|---|---|---|
| 2,494,464 | 1/1950 | Vivie et al. | 30/43.6 |
| 2,802,260 | 8/1957 | Allen | 30/43.6 X |
| 3,381,373 | 5/1968 | Brown | 30/43.6 X |
| 3,732,858 | 5/1973 | Banko . | |
| 3,844,272 | 10/1974 | Banko . | |
| 3,937,222 | 2/1976 | Banko . | |
| 3,945,375 | 3/1976 | Banko | 606/170 X |
| 3,976,077 | 8/1976 | Kerfoot, Jr. . | |
| 4,368,734 | 1/1983 | Banko . | |
| 4,598,710 | 7/1986 | Kleinberg et al. | 606/170 |
| 4,679,558 | 7/1987 | Kensey et al. | 606/180 X |
| 4,867,157 | 9/1989 | Burleson et al. | 606/170 |

FOREIGN PATENT DOCUMENTS

81/01363 5/1981 PCT Int'l Appl. .

Primary Examiner—Michael H. Thaler
Attorney, Agent, or Firm—Hoffmann & Baron

[57] ABSTRACT

A method and apparatus are provided for removing gelatinous tissue, such as cataractous lens tissue, from a patient. A probe-like instrument is provided which includes a thin, perforated plate mounted to an end thereof. A rotatable cutting tool is positioned within the probe and includes a cutting edge which bears against the perforated plate. The plate is moved into contact with a tissue mass, thereby causing portions of the tissue mass to project through the perforations in the plate. Rotation of the cutting tool causes the tissue mass to be sheared into small fragments which can be removed by aspiration.

17 Claims, 1 Drawing Sheet

METHOD AND APPARATUS FOR REMOVING GELATINOUS TISSUE

BACKGROUND OF THE INVENTION

1. Field of the Invention

The field of the invention relates to methods and apparatus for removing gelatinous or other relatively soft tissue during a surgical procedure.

2. Brief Description of the Prior Art

The presence of certain types of soft tissue masses in the body often necessitates surgery. Lens tissue, which is generally a clear, transparent tissue located posterior to the pupil and iris, should be removed if it becomes opaque or milk-white in appearance. This condition is known as cataract, and can cause partial or total blindness.

A number of different techniques have been employed for removing cataractous tissue. U.S. Pat. No. 3,589,363 discloses a method for removing cataracts known as phacoemulsification. An ultrasonically vibrated tool is used in this method to break up the cataractous tissue. The tissue is then aspirated out of the eye by means of a suction device. An instrument for performing phacoemulsification is disclosed in U.S. Pat. No. 4,634,420. A small limbal incision, preferably three to four millimeters in length, is made into the anterior chamber of the eye if this instrument is employed.

Other types of cutting instruments are also known for performing surgery. U.S. Pat. No. 3,945,375 discloses an instrument for removing tissue which includes a fluted cutter drill housed in a probe. In use, the probe is inserted within an incision and the cutter drill caused to rotate with respect to the shearing edges of an opening in the probe. Suction is applied through the probe to draw tissue into the opening. A shearing cut is made between the cutter drill and the opening, and the tissue is removed through a passage within the probe.

Other types of surgical cutting instruments are disclosed in U.S. Pat. Nos. 3,732,858, 3,844,272, 3,937,222, 3,976,077, and 4,368,734.

SUMMARY OF THE INVENTION

It is an object of the invention to provide an instrument capable of cutting soft tissue in an efficient manner.

It is another object of the invention to provide a surgical cutting instrument which requires only a small incision for insertion within the body.

A still further object of the invention is to provide a surgical cutting instrument including means for removing tissue fragments as they are cut.

In accordance with these and other objects of the invention, a surgical instrument is provided which comprises a body portion, a thin, perforated end piece mounted to the body portion, and a rotatable cutting blade positioned within the body portion and in juxtaposition to the perforated end piece. The cutting blade preferably includes a cutting edge which conforms, at least in part, to the shape of the perforated end piece. The perforated end piece may have a flat or concave configuration. It is preferably oriented substantially perpendicularly with respect to the longitudinal axis of the body portion. Means may be provided for aspirating fragmented tissue through the body portion of the instrument. Means may also be provided for irrigating the site of the operation.

A method for removing soft tissue is also provided by the invention. The method includes the steps of providing a cutting instrument including a thin, perforated end and a rotatable cutting blade having a cutting edge adjoining and conforming, at least in part, to said perforated end, contacting a soft tissue mass with said perforated end of said instrument such that part of said soft tissue mass is moved within said perforations, and rotating said blade such that said part of said tissue mass is sheared off by said cutting blade. The tissue fragments sheared off by the instrument are preferably removed through the instrument via aspiration.

BRIEF DESCRIPTION OF THE INVENTION

DETAILED DESCRIPTION OF THE INVENTION

Figure 1:
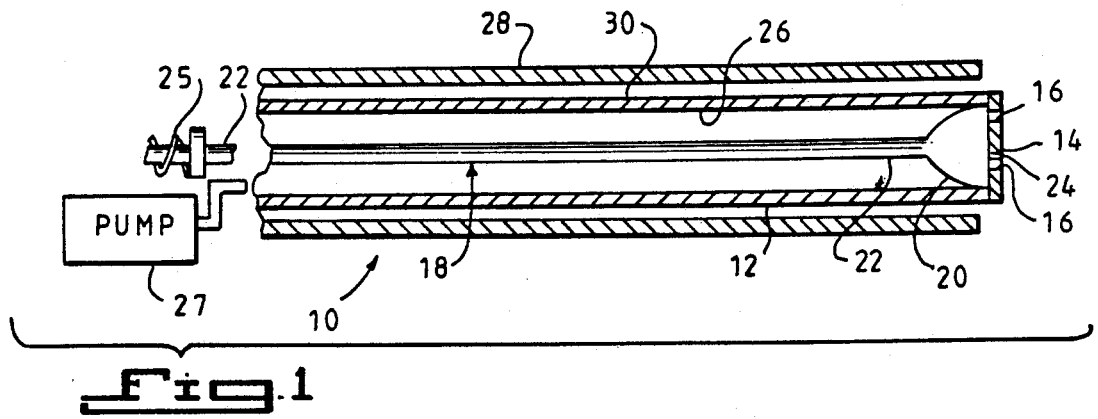
FIG. 1 is a sectional, side elevation view of an instrument for cutting and removing soft tissue.
Figure 2:
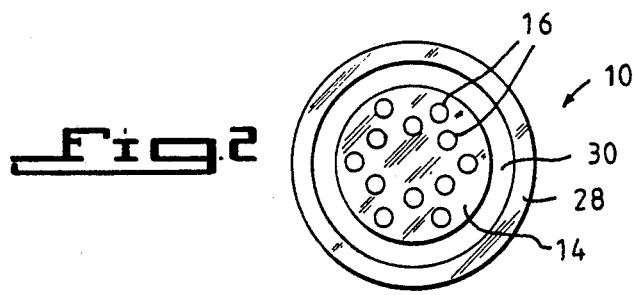
FIG. 2 is an enlarged end view thereof.

An instrument 10 for cutting and removing soft tissue, such as cataractous lens tissue, is shown in FIGS. 1-2. The instrument includes a hollow, cylindrical body 12 made from stainless steel or other relatively inert material. A cannula having a diameter of less than about fifty mils, forty mils (one millimeter) being preferred. A thin, perforated end plate 14 is mounted to one end of the instrument body. The plate is preferably less than twenty mils in thickness, ten to fifteen mils being preferred, and includes a plurality of apertures 16 therein. Each aperture has a diameter which is preferably less than about five mils in diameter so as to admit only gelatinous tissue and liquids. The plate should be as thin as possible so that the edges defining each aperture are relatively sharp. In addition, soft tissue in contact with the plate should be able to extend, in part, through the apertures so that it may be cut in the manner described hereafter.

A cutting tool 18 comprising a cutting head 20 and a shaft 22 is positioned within the cylindrical body 12, and is rotatable and slidable therein. The cutting head 20 includes one or more cutting edges 24 which conform to the shape of the end plate 14. These edges abut the end plate. A spring 25 or the like may be provided for resiliently urging the cutting head against the end plate.

The cutting head 20 has a configuration which allows the flow of material through the apertures 16 and into the bore 26 of the cylindrical body 12. In the embodiment shown in FIG. 1, the head has a generally planar configuration. The end of the head portion includes a concave groove which forms a pair of parallel cutting edges.

A sleeve 28 is mounted in concentric relation to the cylindrical body 12. The inner wall of the sleeve 28 and the outer wall of the cylindrical body define an annular passage 30 through which fluid may be supplied to the operating site. The cylindrical body 12 and end plate 14 extend a selected distance beyond the sleeve 28. The diameter of the sleeve is preferably less than about sixty mils to minimize the size of the incision necessary for using the instrument.

Means, such as an electric motor, are provided for rotating the shaft 22 about its axis. The cutting head 20 is thereby rotated with respect to the end plate 14. The bore 26 is connected to a vacuum source, such as a peristaltic pump 27, while irrigation fluid is fed through passage 30. A gravity feed is generally adequate for providing this fluid.

Figure 3:
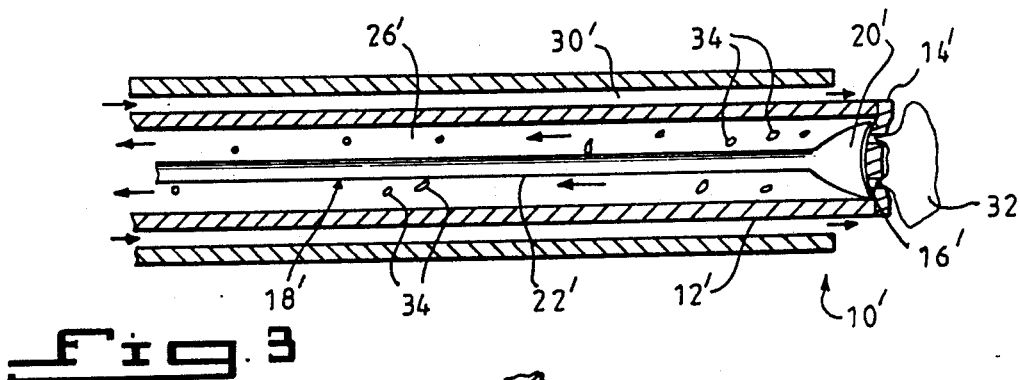
FIG. 3 is a sectional side elevation view of a preferred embodiment of the invention as used to shear and remove a mass of sift tissue.
Figure 4:
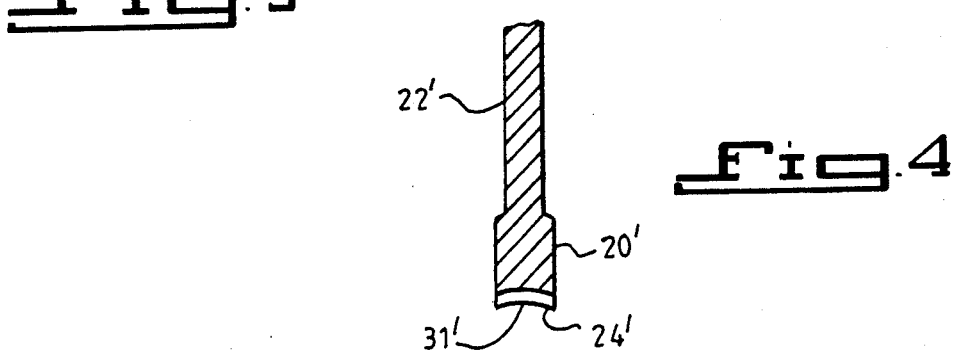
FIG. 4 is a sectional view of a cutting blade in the embodiment shown in FIG. 3.

A generally preferred embodiment of the invention is shown in FIGS. 3-4. The instrument 10' is substantially identical in structure and function to that shown in FIGS. 1-2. It includes a hollow, cylindrical body 12', a thin, perforated end plate 14' secured to the body 12', the end plate including a plurality of apertures 16', and a cutting tool 18' comprising a cutting head 20' and a shaft 22' within the cylindrical body 12'. Unlike the previously discussed embodiment, the end plate 14' includes a concave central portion which extends slightly within the cylindrical body 12'. The cutting edges 24' of the cutting tool 18' have a similar concave shape, as best shown in FIG. 3. FIG. 4, in which the cutting tool 18' is rotated ninety degrees from the position shown in FIG. 3, shows a concave groove 31' and parallel concave cutting edges 24' defined by the end of the cutting head.

The operation of the cutting instruments 10, 10' according to the invention is best shown in FIG. 3. An incision (not shown) of sufficient size to accommodate the end of the instrument shown in the figure is made in the body. The probe-like end of the instrument is inserted through the incision and the end plate 14' positioned against a soft, gelatinous tissue mass 32 which the surgeon wishes to partially or completely remove. Irrigation fluid is supplied through the annular passage 30' while a corresponding amount of material is removed through the bore 26' of the cylindrical body 12'. The pressure of the end plate against the tissue mass 32, combined with the suction applied to the bore 26', causes a portion of the tissue mass to be drawn through the apertures 16' and into the bore 26'. (The thicknesses of the plates 14, 14' are exaggerated in the drawings. They are actually very thin, as described above, so that the soft tissue easily penetrates through the apertures). The cutting tool 18' is rotated about the axis of its shaft 22', thereby causing the cutting edges 24' to shear off fragments 34 of the tissue mass. These fragments 34 are carried away from the operation site in a well known manner. The instrument is removed and the incision sutured following completion of the operation.

It will be appreciated that various changes can be made to the above embodiments of the invention. The cutting head, for example, can be constructed in a number of different ways so long as it includes cutting edges which abut the end plate. While a pair of parallel cutting edges are shown, the end of the cutting head may be configured to include a fewer or greater number of such edges. In addition, the edges may be oriented at an angle with respect to the plate to provide greater shearing capability. The cutting edges may be integral with the cutting head, as shown, or be defined by cutting blades secured to the cutting head. Although not preferred, the perforated plate and cutting edges may be convex, rather than flat or concave as shown. They may also be oriented differently than shown such that shearing is accomplished by oscillatory, rather than the preferred rotational movement of the cutting edges with respect to the end plate. The end plate may be a separate element, as shown, or an integral part of the cylindrical body. In either case, it should have a sufficiently small width that gelatinous tissue is able to penetrate through the apertures therein.

The invention allows gelatinous tissue to be removed from the body in a safe manner, and requires only a small incision. Unlike certain other cutting methods, little or no heat is generated at the site of the incision.

Although illustrative embodiments of the present invention have been described herein with reference to the accompanying drawings, it is to be understood that the invention is not limited to those precise embodiments, and that various other changes and modifications may be effected therein by one skilled in the art without departing from the scope or spirit of the invention.

What is claimed is:

1. An instrument for removing gelatinous tissue and the like from a body, comprising:
   a hollow, cylindrical body of small diameter having an open end;
   a thin, perforated end piece mounted to said open end of said hollow, cylindrical body, said end piece including a concave portion extending within said hollow cylindrical body and having a plurality of small apertures extending therethrough, said end piece being sufficiently small in width that gelatinous tissue is able to extend through said apertures when pushed against said end piece;
   a cutting tool movably mounted within said hollow cylindrical body, said cutting tool including a cutting edge abutting said thin, perforated end piece and substantially conforming to the inner surface of said perforated end piece;
   means for aspirating materials through said perforated end piece and said hollow, cylindrical body, and
   means for providing irrigation fluid adjacent to said perforated end piece,
   said cutting edge being positioned with respect to said end piece such that it will shear off gelatinous tissue or the like upon the penetration of said tissue through said apertures and movement of said cutting tool.

2. An instrument as defined in claim 1 wherein said end piece is oriented substantially perpendicularly with respect to the longitudinal axis of said hollow, cylindrical body.

3. An instrument as defined in claim 2 wherein said end piece is a plate having a thickness of less than twenty mils.

4. An instrument as defined in claim 2 wherein said cutting tool is rotatably mounted within said hollow, cylindrical body.

5. An instrument as defined in claim 1 wherein each of said apertures has a diameter of less than about five mils.

6. An instrument as defined in claim 1 wherein said hollow, cylindrical body has an outside diameter of less than about forty mils.

7. An instrument as defined in claim 1 including means for resiliently urging said cutting edge into engagement with said end piece.

8. An instrument as defined in claim 1 including a sleeve, said hollow, cylindrical body being positioned within said sleeve, said sleeve and said hollow, cylindrical body defining a substantially annular passage therebetween.

9. An instrument as defined in claim 1 wherein said cutting tool is rotatably mounted within said hollow, cylindrical body.

10. A method for cutting a soft tissue mass within a body, comprising:

providing a cutting instrument including a hollow, probe-like body having an open end, a thin, perforated plate secured to said open end of said body and a cutting edge positioned within said body and abutting said plate, said plate including a plurality of small apertures extending therethrough and a concave portion extending within said body;

providing an incision within the body;

inserting at least part of said body through said incision;

contacting said soft tissue mass with said concave portion of said plate such that part of said tissue mass extends through at least some of said apertures within said plate, and moving said cutting edge with respect to said plate, thereby shearing off said part of said tissue mass extending through said apertures in said plate and forming tissue fragments therefrom.

11. A method as defined in claim 10 wherein said tissue is cataractous lens tissue.

12. A method as defined in claim 10 including the step of applying suction to a side of said plate opposite from said tissue mass, thereby drawing said tissue fragments away from said plate.

13. A method as defined in claim 10 including the step of rotating said cutting edge about an axis.

14. A method as defined in claim 10 including the step of providing irrigation fluid through said incision.

15. A method as defined in claim 10 wherein said plate has a thickness of less than twenty mils.

16. A method as defined in claim 10 wherein each of said apertures has a diameter of less than five mils.

17. A method as defined in claim 10 including the step of applying suction within said hollow, probe-like body.

* * * * *